United States Patent [19]

Vermeer et al.

[11] Patent Number: 5,100,798
[45] Date of Patent: Mar. 31, 1992

[54] METHOD FOR THE EXTRACTION OF A VITAMIN-K-DEPENDENT CARBOXYLASE COMPLEX AND THE USE THEREOF

[75] Inventors: Cornelis Vermeer, Maastricht; Berry A. M. Soute, Schimmert, both of Netherlands

[73] Assignee: Rijksuniversiteit Limburg, Maastricht, Netherlands

[21] Appl. No.: 112,603

[22] PCT Filed: Jan. 27, 1987

[86] PCT No.: PCT/NL87/00002
§ 371 Date: Oct. 27, 1987
§ 102(e) Date: Oct. 27, 1987

[87] PCT Pub. No.: WO87/04719
PCT Pub. Date: Aug. 13, 1987

[30] Foreign Application Priority Data
Jan. 29, 1986 [NL] Netherlands ............ 8600206

[51] Int. Cl.$^5$ ............................................. C12N 9/88
[52] U.S. Cl. .................................................. 435/232
[58] Field of Search ........................................ 435/232

[56] References Cited

PUBLICATIONS

Girardot, "Vitamin K-Dependent Carboxylase: Partial Purification and Properties of the Enzyme-Substrate Complex", J. Biol. Chem. 257(24), 15008–15011, 1982.
"Vitamin K-Dependent Carboxylase: Evidence for Cofractionation of Carboxylase and Epoxidase Activities, and for Carboxylation of a High-Molecular-Weight Microsomal Protein", Chemical Abstracts, vol. 96, No. 17, Apr. 26, 1982, Summary No. 138618w, Wallin et al., p. 370.
"Vitamin K-Dependent Carboxylation: Synthesis and Biological Properties of Diastereomeric Gamma-Substituted Glutamic Acid Containing Peptidic Substrates", Biological Abstracts, vol. 79, No. 6, 1985, Summary No. 46413, Bory.
"Vitamin K-Dependent Carboxylase: Partial Purification and Properties of the Enzyme-Substrate Complex", Biological Abstracts, vol. 75, No. 11, 1983, Summary No. 79838, Girardot.
"Isolation and Characterization of a cDNA Coding for Human Factor IX", Proc. Natl. Acad. Sci. USA, Biochemistry, vol. 79, Nov. 1982, Kurachi et al., pp. 6461–6464.
"Characterization of the Complementary Deoxyribonucleic Acid and Gene Coding for Human Prothrombin", Biochemistry, vol. 22, No. 9, 1983, Degen et al., pp. 2087–2097.
"Characterization of Bovine Prothrombin mRNA and Its Translation Product", Biochemistry, vol. 23, No. 8, 1984, MacGillivray et al., pp. 1626–1634.
"Vitamin K-Dependent Carboxylase", Haematologia, vol. 18, No. 2, 1985, Vermeer et al., pp. 71–97.
"A Comparison Between Vitamin K-Dependent Carboxylase from Normal and Warfarin-Treated Cows", Biochimica et Biophysica Acta, 1982, Vermeer et al., pp. 361–365.
"Partial Purification of Bovine Liver Vitamin K-Dependent Carboxylase by Immunospecific Adsorption onto Antifactor X", FEBS Letters, vol. 123, No. 2, Jan. 1981, De Metz, pp. 215–218.
"Vitamin K-Dependent Carboxylase: The Carboxylation of Exogenous Substrates in Different Systems", Biochimica et Biophysica Acta, 1985, de Boer-van den Berg et al., pp. 1–5.
Hubbard et al., Proc. Natl. Acad. Sci. USA, vol. 86, Sep. 1989, pp. 6893–6897.
Soute et al., Thrombosis and Haemostasis, vol. 61, 1989, pp. 238–242.

Primary Examiner—Douglas W. Robinson
Assistant Examiner—Jean C. Witz
Attorney, Agent, or Firm—Young & Thompson

[57] ABSTRACT

Method for the extraction and insolubilization of a vitamin-K-dependent carboxylase complex from biological material, for instance a bovine liver homogenate, which can be used for the conversion of, for example, precursors of the blood coagulation factors II, VII, X and especially IX prepared via recombinant DNA-technology, the insolubilized carboxylase complex, as well as the prepared biologically active blood coagulation factors to be used in pharmaceutical compositions.

6 Claims, No Drawings

METHOD FOR THE EXTRACTION OF A VITAMIN-K-DEPENDENT CARBOXYLASE COMPLEX AND THE USE THEREOF

The invention relates to a method for the extraction of a vitamin-K-dependent carboxylase complex from biological material which can be used for the conversion of, for example, blood coagulation factor IX precursors prepared via recombinant DNA technology, into the blood coagulation factor IX.

As is known, patients who lack the blood coagulation factor IX suffer from haemophilia B. As a possibility of helping these patients concentrates of these coagulation factors are nowadays made on a large scale, which concentrates are extracted from human blood plasma. However, many kinds of difficulty are associated with the injection of human blood products in patients. As difficulties, mention may be made of:

1) the transmission of diseases such as hepatitis and AIDS;
2) the necessity of mounting extensive blood plasma campaigns for the collection of the necessary blood; and
3) the extraction of the respective coagulation factors from human blood plasma is cumbersome and costly.

From Proc. Natl. Acad. Sci. USA, vol. 79, pages 6461–6464, November 1982 and Biochemistry 1983, 22, pages 2087–2097, the possibility is known of isolating and incorporating in bacteria the DNA fragment that codes for factor IX. The said bacteria multiply rapidly and produce at the same time the desired coagulation factor IX, which can be extracted from the culture medium (see Biochemistry 1984, 23, pages 1626–1634). Also eukaryotic cell lines producing recombinant factor IX-like material have been described (Nature 316, 1985, pages 268–270 and pages 271–273, J. Biol. Chem. 261, 1986, pages 9622–9628).

With the above named method the risk of disease transmission is eliminated, there is no dependence on blood donors and, in addition, the production process is cheaper. However, there is still a fundamental problem relating to the coagulation factor IX prepared in this manner. In particular, it is of essential importance for the biological activity of the said factor that it undergoes a so-called post-translational modification. This modification consists of the gamma-carboxylation of the 12 N-terminal glutamic acid residues. As is evident, for example, from Haematologia 18 (2), pages 71–97 (1985), the enzyme which is responsible for this carboxylation reaction is the vitamin-K-dependent carboxylase, which enzyme does not occur in bacteria. Also in eukaryotic cell lines (which do contain carboxylase) the recombinant factor IX is carboxylated for only 1-3% (J. Biol. Chem. 261, 1986, pages 9622–9628). The factor IX referred to above and produced with the aid of DNA recombinant technology is therefore biologically inactive and cannot be used for making up the deficiency in haemophilia B patients. The same problem arises with the uncarboxylated blood coagulation factors II, VII and X produced with the aid of bacteria modified by DNA recombinant technology.

The invention therefore has the object of developing a method of converting uncarboxylated coagulation factors II, VII, X and in particular IX, into the biologically active form. From Biochimica et Biophysica Acta 714 (1982), pages 361–365 it is known that in principle the starting point for the extraction of the carboxylase complex may be two types of liver, preferably bovine liver, namely: (a) normal liver and (b) liver from cows which have previously been treated with vitamin K antagonists. As a result of this treatment uncarboxylated blood coagulation factors accumulate in the liver, where they are complexed with the carboxylase complex. In the case of the normal liver a "substrate-free" enzyme is thus obtained and in the case of animals treated with vitamin K antagonists an enzyme/substrate complex is obtained. This latter complex is very tight and, as far as is known, can only be split by boiling in 10% SDS.

Although the carboxylase is detectable in liver homogenates and in the microsomal fraction therefrom, preparations of this type are too impure to be used for the carboxylation of, for example, the blood coagulation factor IX precursor. Moreover, a so-called "solid-phase" carboxylase is preferably used, the enzyme being coupled to a solid carrier so that the enzyme can readily be removed from the solution after the carboxylation.

In the first attempt of the Applicant, which has been described in FEBS Letters 123 (1981), pages 215–218, the starting point was antibodies which were raised against purified normal coagulation factors from bovine blood. These antibodies were likewise purified, coupled to a solid carrier and used for the extraction of a liver homogenate from cows which had been treated with vitamin K antagonists. The antibodies against the normal coagulation factors also had an affinity for the as yet uncarboxylated substrate molecules. With the aid of the solid-phase antibodies obtained, it was therefore possible to extract the enzyme/substrate complexes specifically from the liver homogenate. The binding under these circumstances took place via the substrate. The solid-phase carboxylase prepared in this manner remained very active in vitro and was capable of carboxylating both the complexed (endogenous) substrate and added (exogenous) substrates. The sequence in which this took place was always first the endogenous and then the exogenous substrate. It is pointed out in this connection that even after carboxylation of the endogenous substrate the enzyme remained bound thereto. The above named solid-phase carboxylase had, however, the disadvantage that only small exogenous substrates could be carboxylated (see inter alia Biochimica et Biophysica Acta 831 (1985), pages 94–98). Since coagulation factor precursors such as the factor IX precursor are large, these were not carboxylated with the aid of the above described solid-phase carboxylase (probably as a result of steric hindrance of the still bound endogenous substrate).

It has been found that the problem outlined above can be eliminated by starting from a substrate-free carboxylase complex for the carboxylation of exogenous substrates. More particularly, the invention relates to a suitable method for the extraction and insolubilisation of a purified vitamin-K-dependent carboxylase complex from biological material wherein a) the biological material containing carboxylase complex is suspended in a neutral buffer which contains a detergent;

b) the suspension is centrifuged and the supernatant liquid removed;

c) the membrane-bound carboxylase complex portion obtained in the centrifuge treatment is taken up in a neutral buffer, which buffer contains a detergent in an increased activity with respect to step (a) and a salt;

d) the suspension obtained in step (c) is centrifuged and e) the supernatant obtained in step (d) is subjected to a precipitation treatment with a salt, a gradient centrifugation and a chromatography treatment.

Preferably the microsomal fraction of bovine liver homogenates, in particular from anticoagulated cattle, is used as the biological material in step (a). Anticoagulated cattle are therefore cattle which have previously been treated with vitamin K antagonists. Moreover, a buffer based on KCl and Tris.HCl with pH of 7.4 is used with advantage as neutral buffer in step (a) and the compound CHAPS (3-(3-cholamidopropyldimethylammoniol)-1-propansulfonate) as detergent.

In the steps (c) and (e) ammonium sulfate is used with advantage as salt. Moreover in the said step (e) a sucrose gradient centrifugation and also a gel permeation chromatography is used.

With the aid of the carboxylase complex considerably purified in this manner, which undoubtedly consists of several proteins but behaves as a single complex, it is possible to induce antibodies in mammals. If the carboxylase complex is prepared from anticoagulated test animals and is therefore injected as enzyme/substrate complex, antibodies are obtained which, after a purification known per se, are capable of specifically and completely precipitating carboxylase from a homogenate of untreated bovine livers. The invention therefore also relates to carrier material which contains antibodies with respect to the carboxylase/substrate complex, these antibodies being bound to a carboxylase complex taken up in the above manner. With particular preference this last named carboxylase complex is substrate-free. With a carrier material of this type containing substrate-free carboxylase complex it is in particular possible to carboxylate large exogenous substrates, in other words with activated carrier materials of this type it is possible to convert microbiologically prepared coagulation factors such as, in particular, factor IX, of which the glutamic acid residues concerned have still to be converted into the gamma-carboxyglutamic acid residues, from the inactive form to the active form.

The examples below serve only to illustrate the invention and should be interpreted as restrictive.

EXAMPLE I

The Preparation of Soluble Carboxylase Complex and of Solid-Phase Carboxylase

From a liver homogenate from cattle the microsomal fraction is prepared by standard methods. These microsomes are resuspended in a buffer which contains 0.5M KCl, 20 mM Tris.HCl (pH: 7.4), and 0.5% (w/v) of the detergent CHAPS. After centrifuging (1 h, 150,000 g) approximately 50% of the carboxylase is in the supernatant. This carboxylase portion is described in accordance with the prior art as the dissolved carboxylase and it has hitherto hardly been possible to purify it further. This supernatant is removed and the treatment is continued with the other portion of the carboxylase, viz. the membrane-bound portion in the pellet of the last centrifuge run. The carboxylase is extracted from this material with a buffer which contains 0.5M KCl, 20 mM Tris.HCl (pH: 7.4), 1% (w/v) CHAPS and 1.5M $(NH_4)_2SO_4$. After a second centrifugation there follows a precipitation with the aid of $(NH_4)_2SO_4$ (the final concentration is 3M), a sucrose gradient centrifugation (gradient of 20–60% sucrose, 40,000 rpm, 18 h) and a gel permeation chromatography on an AcA 44 column. In this manner a "carboxylase complex" is obtained which undoubtedly consists of several proteins but behaves as a single complex.

The carboxylase complex obtained in the above named manner was injected into rabbits to induce antibodies. In this example the starting point was liver homogenates of anticoagulated cattle so that the carboxylase complex was administered as an enzyme/substrate complex. The antibodies, which were obtained in a manner known per se, were capable of precipitating the carboxylase complex from untreated test animals specifically and completely, the carboxylase remaining also completely active as an immune complex.

The above named antibodies were purified in a manner known per se and bound to a solid carrier such as Sephadex. In using these immobilised antibodies for the extraction of carboxylase it emerged that the carboxylase could be obtained in a specific manner from a homogenate of a liver from a cow which had not been treated with vitamin K antagonists. The solid-phase carboxylase prepared in this manner was very well capable of converting large substrates such as coagulation factor precursors obtained via recombinant DNA technology, for example the factor IX precursor from the uncarboxylated form into the mature carboxylated form.

EXAMPLE II

A Continuous-Flow System for the Carboxylation of Exogenous Substrates

The solid-phase carboxylase described in Example I is introduced into a column and connected to a continuous-flow system; the ingredients which are necessary for the carboxylation reaction are: dithiothreitol (5 mM), vitamin K hydroquinone, bicarbonate, molecular oxygen (dissolved in the buffer) and the substrate to be carboxylated such as the factor IX precursor. After injection of the combination, in addition to the used or unused cofactors, the effluent from the column also contains the carboxylated product, viz. factor F IX, which can be isolated in a simple manner.

It emerged that the efficiency of the above named reaction can be raised by a factor of 5–10 by increasing the bicarbonate concentration from the usual 0.7 mM to 50 mM. In this way non-carboxylated recombinant factor IX could be carboxylated and more than 8 gamma-carboxyglutamic acid residues were introduced per molecule of factor IX. It was demonstrated that the incorporated carboxyl group (which was radioactively labeled) was protein-bound, that it could be extracted from solution using specific immobilized antibodies against native factor IX and that after immunoprecipitation the protein-bound label migrated during electrophoresis in polyacrylamide gels as a single band which coincided with native factor IX.

EXAMPLE III

The Carboxylation of Solid-Phase Substrates

After coagulation factor precursors have been produced by bacteria or eukaryotic cells, the precursors have to be extracted from the culture media. The extraction procedures generally applied include the specific binding of the precursors to insoluble matrices such as Sepharose-bound heparin and Sepharose-bound antibodies. The coagulation factor precursors as well as other carboxylatable substrates may be carboxylated when they are bound to the insoluble matrices. The ingredients required for the carboxylation reaction are similar to those described in example II except that solid-phase carboxylase is replaced by the soluble carboxylase complex. In this way a number of substrates have been carboxylated and in particular the large protein substrates (like the factor IX-precursor) were carboxylated to a similar degree as in example II.

We claim:

1. A method for the extraction of a vitamin-K-dependent carboxylase complex from biological materials, comprising
    a) suspending biological material containing carboxylase complex in a neutral buffer which contains a detergent,
    b) centrifuging the suspension and removing the supernatant liquid from the precipitated membrane-bound carboxylase complex portion,
    c) suspending the precipitated membrane-bound carboxylase complex portion obtained in the centrifuge treatment in a neutral buffer which contains 3-[(3-cholamidopropyl)dimethylammoniol]-1-propansulfonate as a detergent, said neutral buffer of step (c) having an increased detergent activity with respect to said neutral buffer of step (a), and ammonium sulphate,
    d) centrifuging the suspension obtained in step (c) and
    e) subjecting the supernatant obtained in step (d) to a precipitation treatment with ammonium sulphate, a gradient centrifugation and a chromatography treatment.

2. The method according to claim 1, characterised in that the microsomal fraction of bovine liver homogenates is used in step (a) as biological material.

3. The method according to claim 2, characterised in that the microsomal fraction of liver homogenates of anti-coagulated cattle is used in step (a) as biological material.

4. The method according to claim 1, characterised in that a buffer comprising KCl and Tris.HCl with a pH of 7.4 is used in step (a) as neutral buffer.

5. The method according to claim 1, characterised in that 3-[(3-cholamidopropyl)dimethylammoniol]-1-propansulfonate is used in step (a) as detergent.

6. The method according to claim 1, characterised in that the gradient centrifugation with sucrose is carried out in step (e) and a gel permeation chromatography is used as the chromatography treatment.

* * * * *